United States Patent [19]

Vaillancourt

[11] Patent Number: 4,655,750
[45] Date of Patent: * Apr. 7, 1987

[54] CLOSED SYSTEM CATHETER WITH GUIDE WIRE

[75] Inventor: Vincent L. Vaillancourt, Livingston, N.J.

[73] Assignee: Manresa, Inc., Hillsdale, N.J.

[*] Notice: The portion of the term of this patent subsequent to Jun. 25, 2002 has been disclaimed.

[21] Appl. No.: 800,817

[22] Filed: Nov. 22, 1985

[51] Int. Cl.$^4$ .............................................. A61M 5/18
[52] U.S. Cl. ................................... 604/165; 604/168; 604/171; 604/52
[58] Field of Search ...................... 604/52–53, 604/164–165, 168–169, 171, 173, 177

[56] References Cited

U.S. PATENT DOCUMENTS

| 2,915,063 | 12/1959 | Cutter | 604/163 |
| 4,326,520 | 4/1982 | Alley | 604/171 |
| 4,525,157 | 6/1985 | Vaillancourt | 604/52 |
| 4,563,176 | 1/1986 | Gustavsson et al. | 604/171 |

FOREIGN PATENT DOCUMENTS 2110009  5/1972  France ............................ 604/171

OTHER PUBLICATIONS

"A Method for Ureteric Catheterisation", The Lancet, p. 557, Sep. 14, 1963.

Primary Examiner—C. Fred Rosenbaum
Assistant Examiner—Gene B. Kartchner
Attorney, Agent, or Firm—Ralph R. Roberts

[57] ABSTRACT

A catheter system is provided for the introduction and placement of a flexible catheter into the lumen of an artery or vein. A guide wire is provided and is kept in a sterile condition within a flexible bag-like enclosure attached to the hub of a needle. The needle is hollow and is sharpened in the usual manner and is secured in a hub to provide a needle assembly. This hub is provided with a skirt and extends through this hub and into flow communication with a "flashback" chamber. In one embodiment, the needle is connected to a tubular member having a transverse hole near its interior end, and in another embodiment the needle's inner end is in flow communication with a channel or annular groove in a centering plug. In every embodiment, there is a centering plug which provides a guideway for the guide wire which is positioned in this guideway to prevent fluid flow. The guide wire is manipulated forwardly by grasping the wire through the bag-like enclosure and advanced forwardly by "feel" and into the lumen after penetration has been made as indicated by the "flashback." The catheter is separated from the needle hub and advanced along the guide wire until placement is achieved, after which the needle, guide wire and bag are withdrawn from the patient and discarded.

27 Claims, 18 Drawing Figures

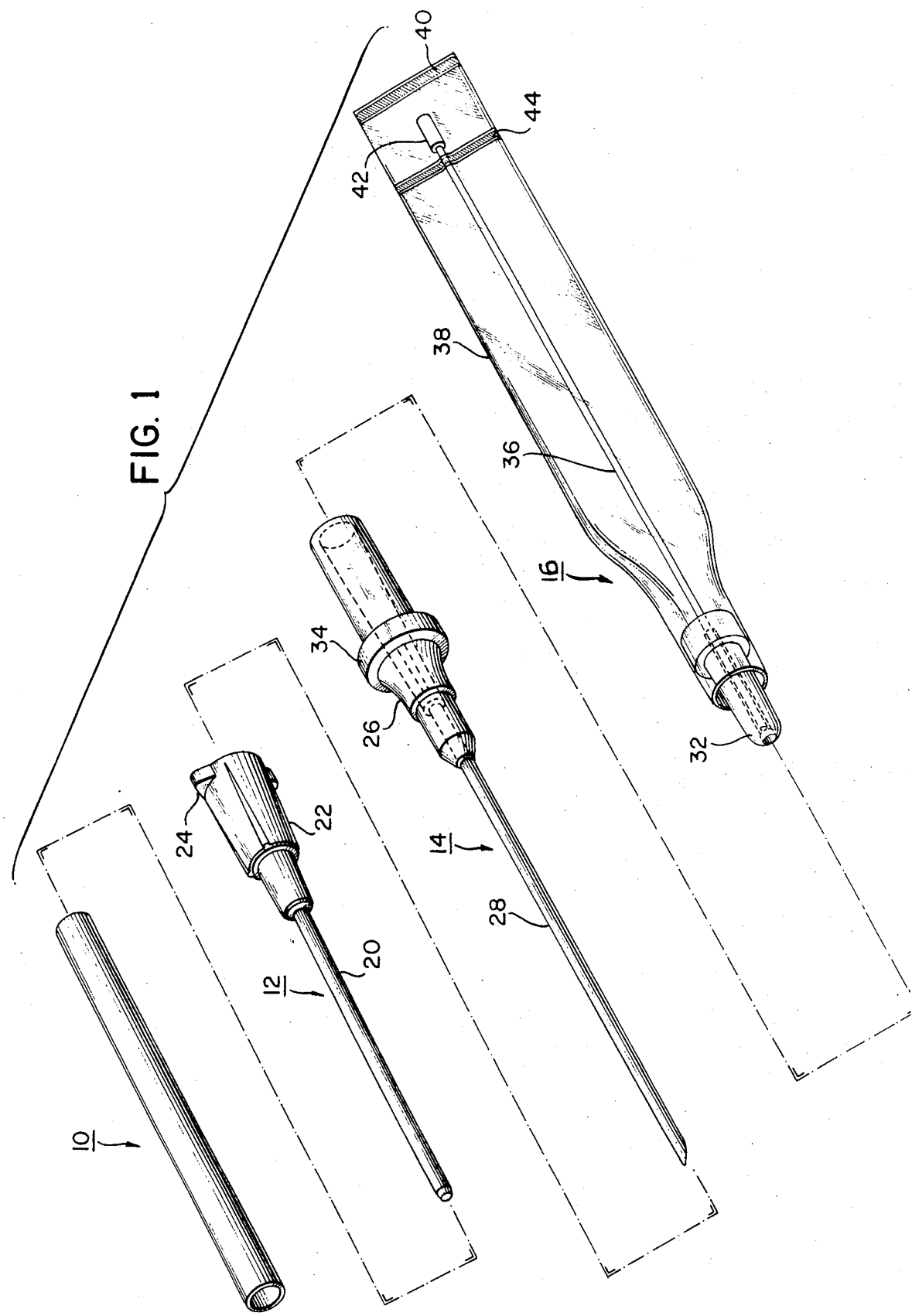

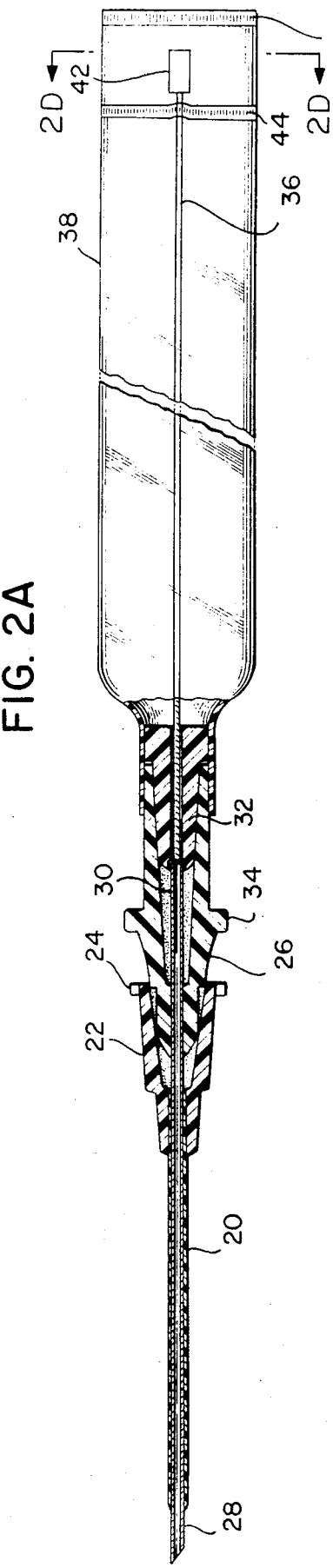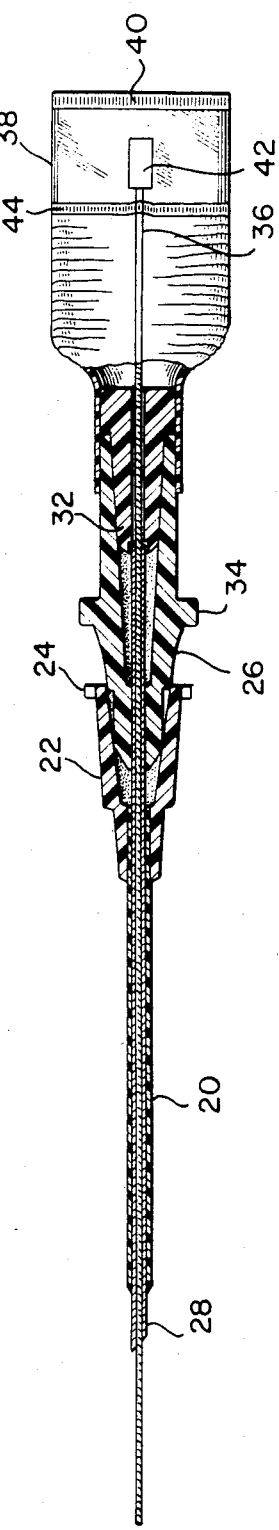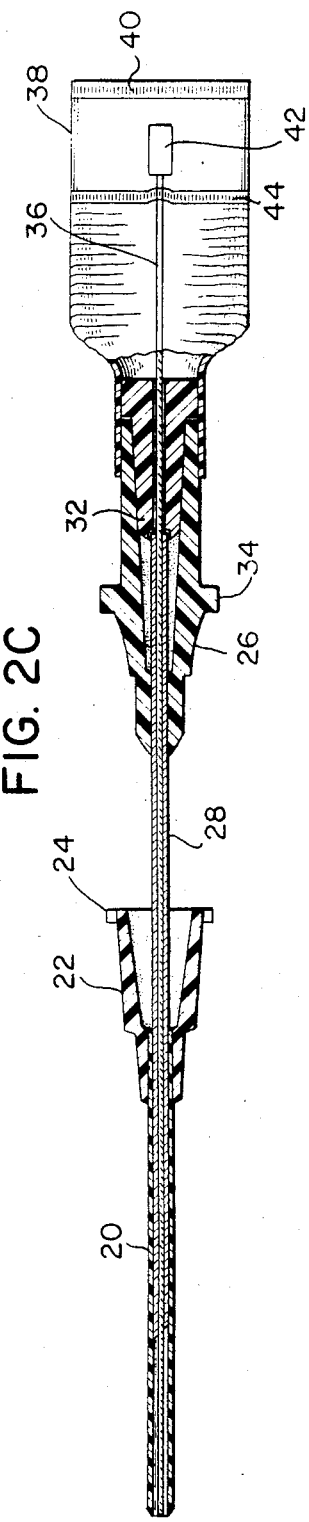

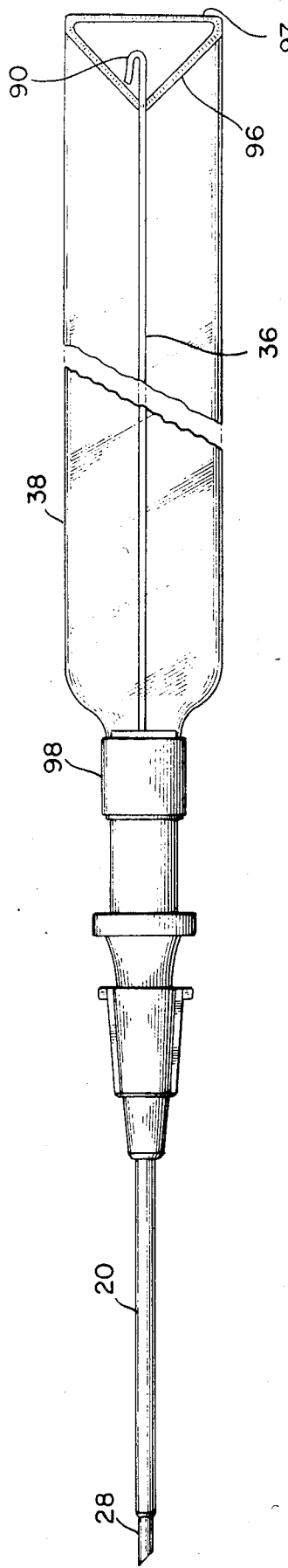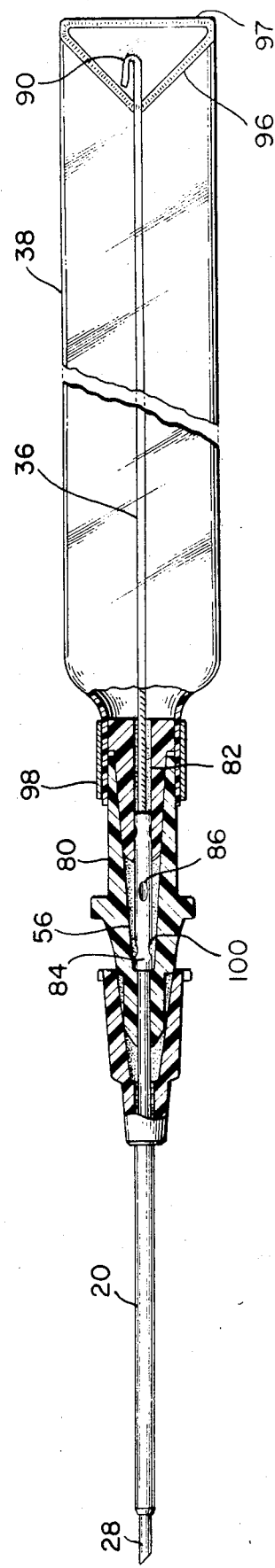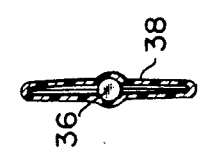

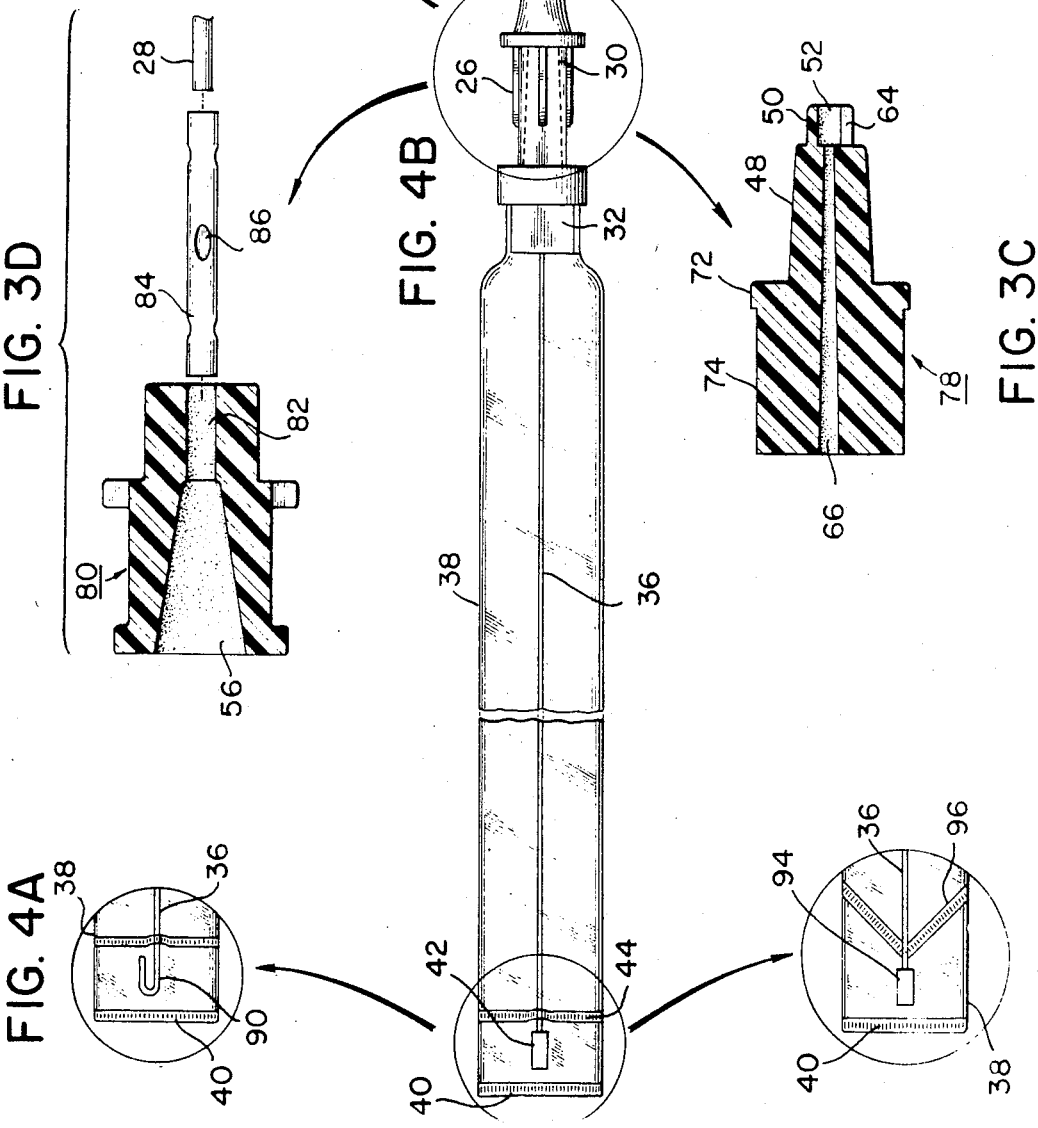

CLOSED SYSTEM CATHETER WITH GUIDE WIRE

CROSS-REFERENCE TO RELATED PATENTS

This application pertains to a closed system catheter with guide wire as shown in the patent having Ser. No. 518,122 and filed July 28, 1983. This application matured as U.S. Pat. No. 4,525,157, issuing June 25, 1985. To the extent applicable, this patent is incorporated by reference into this application. A Terminal Disclaimer is filed herewith to obviate a double patenting rejection. This terminal disclaimer and the fee for said filing are in accordance with rule No. 1.321 (b) and the fee for the small entity of $25.00 as per No. 1.20 (d) is enclosed. Any patent issuing on this application will terminate June 25, 2002.

BACKGROUND OF THE INVENTION

1. Field of the Invention

With reference to the classification of art as established in and by the U.S. Patent Office, this invention is believed to be found in the field pertaining to "Surgery" and particularly to "flexible catheter guide."

2. Description of the Prior Art

Arterial blood infusion and withdrawal devices are known and the technique of a guide wire inserted into the lumen of the artery is known and shown as prior art in FIGS. 1A through 1C to be hereinafter more fully discussed. A catheter placement system is shown in U.S. Pat. No. 3,416,531 to Edwards, as issued Dec. 17, 1968; a guide for the catheter is also shown in U.S. Pat. No. 3,547,103, as issued to Cook on Dec. 15, 1970; a flashback indicator is shown in U.S. Pat. No. 3,942,514, as issued to Ogle on Mar. 9, 1976; a withdrawal system using a guide wire is shown in U.S. Pat. No. 4,006,743, as issued to Kowarski on Feb. 8, 1977; a cetheter placement assembly is shown in U.S. Pat. No. 4,046,144 to McFarlane, as issued Sept. 6, 1977; an extraction device is shown in U.S. Pat. No. 4,215,702, as issued to Mayer on Aug. 5, 1980; a blood collecting device with indicator is shown in U.S. Pat. No. 4,154,229, as issued to Nugent on May 15, 1979; a needle and sheath are shown in U.S. Pat. No. 4,230,123, as issued to Hawkins, Jr. on Oct. 28, 1980, and a guide wire placement is shown in U.S. Pat. No. 4,274,408, as issued to Nimrod on Jan. 23, 1981.

Of particular note is U.S. Pat. No. 4,417,886 to Frankhouser et al, as issued Nov. 29, 1983. In this patent, in addition to Hawkins and Nimrod noted above, are referenced U.S. Pat. No. 3,995,628 to Gula; U.S. Pat. No. 4,068,659 to Moorehead; U.S. Pat. No. 4,068,660 to Beck; U.S. Pat. No. 4,205,675 to Vaillancourt; and U.S. Pat. No. 4,306,562 to Osborne. In the Frankhouser disclosure, it is particularly noted the necessity of using an elongated tubular member connected to and projecting rearwardly from the proximal end of the needle. This tubular member is of a transparent, semi-rigid plastic material. Although the plastic material may have some flexibility, it should have sufficient resilience so that it maintains its tubular configuration in use. This disclosure continues: "In its preferred form, tubular member has a longitudinally extending slot running from a point adjacent the needle hub." An extending handle is adapted to be moved in this slot in the tubular member, with this handle attached to the guide wire to produce the desired movement. The Frankhouser showing does not employ an arrangement which would lend itself to or suggest a closed system with product sterility being maintained after removing the outer package or during advancement of the guide wire in the catheter.

Although the present apparatus may be used in both veins and arteries, penetration into the artery is the most difficult and requires the greater expertise. The preferred arterial catheter insertion site is the radial artery immediately proximal to the wrist. This site is preferred because the artery is relatively close to the skin and therefore relatively accessible. The position and orientation of the artery is normally located by detecting the pulse and following the pulse beat up the artery for about one inch or more in length. Some practioners draw an ink line on the skin to show this position and orientation. The catheter and needle assembly is then introduced at an angle about thirty to forty-five degrees to the surface of the skin, with the bevel of the needle facing up, or toward the outer surface.

This method of insertion is a real challenge even to the most experienced practitioner. First, he must find the artery with the point of the introducer needle and obtain flashback through the hollow of the introducer needle. Many practitioners remove the existing flash plugs in hopes of being able to obtain a quicker flashback (indication of piercing the artery). These practitioners desire a quicker flashback in the hope that this will indicate entry into the artery before penetration through the back wall of said artery with the needle point.

The artery wall is both thick (to support arterial blood pressure) and elastic and as a result the needle significantly compresses or dimples the artery wall before penetration is achieved. When the needle finally penetrates the first wall the pressure in the artery causes the wall to pop back along the needle, leaving minimal resistance to further forward travel of the needle. The most common occurrence is for the point of the needle to bury itself in the back wall of the artery when the first wall of the artery "pops" back over the heel of the bevel and along the shank of the needle. To compensate for this, some practitioners actually twist the introducer needle about its axis after they have observed flash in the introducer hub. This maneuver is intended to orient the main bevel angle parallel to the back wall of the artery and lift the embedded point out of the back wall. Other practitioners tend to draw the introducer needle back after they see flashback on the assumption that the point is embedded into the back wall of the artery.

Once the practitioner has observed flashback in the introducer and has been able to slide the catheter forward a short distance on the introducer, he assumes that he is in the artery with the tip end of the catheter. At this point, however, it is not just a simple matter of sliding the entire assembly or the catheter alone up the artery as the axis of the introducer needle is disposed at a substantial angle to the axis of the artery. This needle, when and as positioned, cannot be advanced up an artery or vessel. Rather, the practitioner utilizes a delicate feel to slide the catheter off of the introducer needle and into and up the artery. This procedure requires the advancing catheter to bend at its point of entry into the artery. Many times the catheter becomes embedded in the wall of the artery and the practitioner must detect this problem by the feel of the catheter as the catheter is slid forward. If the practitioner does not follow this procedure a substantial risk of gouging the lining of the artery and inducing a severe thrombosis occurs.

In order to get the catheter into the artery the catheter is bent so as to follow the artery. At this point the practitioner usually retracts and readvances the introducer several times during each insertion and puncture of the artery. Each placement may entail half a dozen unsuccessful attempts. Each failed attempt further aggravates the problem, because the artery goes into "spasm." After a few unsuccessful attempts, the user gives up using the catheter unit in the started attempt and with a fresh new unit begins again. In a sampling of hospitals it was found that over two needle-catheter units were used to achieve each successful catheter placement as a further indication of how difficult it is to successfully place catheters in the artery.

SUMMARY OF THE INVENTION

This invention may be summarized, at least in part, with reference to its object. It is an object of this invention to provide, and it does provide, a novel and improved needle inserting device for gaining access to blood vessels, particularly arteries. The needle is hollow and is carried within a catheter secured to a hub. The needle is secured to this hub and carries within its bore a guide wire that is selectively movable. The guide wire is retained within a flexible bag so that contamination is excluded.

It is a further object of this invention to provide, and it does provide, a needle within a catheter, said needle having a sharpened entering point by which penetration of a vessel may be and is achieved. The needle is tubular and at its rear end discharges into a flashback (clear or translucent hub) indicator. A flexible and impervious bag is secured to the hub carrying the needle and enclosing the guide wire so that a sterile field of environment is provided and the guide wire may be moved into the blood vessel without a need for gloves, mask, gowning, etc., under aseptic conditions and contamination-free.

It is a further object of this invention to provide, and it does provide, an improved needle and catheter in which the catheter is carried by a hub and the needle is carried by a separate hub that is separable from the catheter hub. This needle is tubular and is disposed to carry a guide wire attached to the rear end of the flexible and impervious bag. This restraint provides means to prevent unwanted movement of the wire while still providing manipulative (advancement movement of the wire within the needle and/or catheter. The needle is adapted for conducting blood, after penetration of the vessel, so that an immediate flashback is detected. The guide wire is carried within and is manipulated while in a flexible and closed lay-flat tubular bag attached to the needle hub.

The prior art devices do not provide and maintain a sterile environment during manipulative use of the guide wire to place the catheter in a vein or artery. In particular, the Frankhouser patent, identified above, has the guide wire manipulated and advanced by a handle which is moved in and along a slot. As to be more fully disclosed and shown, the guide wire of Applicant's device is advanced by gripping the guide wire between the thumb and fingers of the user and advancing same into the vessel.

In brief, there is depicted a flexible catheter having a selected bore. The entering end of the catheter is chamfered for easy entrance of the catheter into a body opening and then into a penetrated blood vessel (artery or vein). The hub carrying the catheter has a tapered recess for receiving the male luer connector of an administration set such as is used in arterial pressure monitoring. A needle is disposed within and axially aligned with the catheter. The sharpened end extends beyond the catheter to effect penetration. The opposite end is secured to a plastic hub. This needle hub has its outer end portion sized and shaped to be retained within the socket in the catheter hub. The needle has a rearwardly-extending portion that is within a cavity portion of the hub and is proximate the forward end of a centering plug.

This embodiment also provides a product which is not bulky, heavy or cumbersome and therefore allows the practitioner to maintain control of the insertion process through "feel," which is a very vital part of any blood vessel (especially artery) entering procedure. This "feel" is achieved by (1) minimizing the weight of the device, (2) providing a flexible end (bag and wire guide) which maintains good balance in the device, and (3) allowing the practitioner to "feel" the wire guide as it is advanced. By gripping the guide wire through the bag, which is very thin and supple, the user's sense of "feel" is utilized during advancement. The guide wire is usually grasped about one-half to one inch from the centering plug and advanced (moved forwardly) in small increments in and with repeated steps until the guide wire advancement limit or extent is reached.

As far as is known, this closed system catheter with guide wire has advantages over prior products and among other advantages include: (1) providing a catheter introduction system which has all the "feel" advantages of a "typical" Intravenous Catheter, (2) providing an entry point for a guide wire without blood leakage, (3) the advancement of the guide wire into the blood vessel under closed system (sterile) conditions, (4) the sizing by the needle of the entrance opening to the blood vessel sufficient to allow the movement of the catheter into it, (5) the advancement of the catheter into the vessel under conditions that will not injure the vessel wall and being positively guided as to where it should go, and (6) the removal of all components other than the catheter which remains in place in a sterile manner maintaining a closed system until the moment of hook-up to the pressure monitoring system, administration set, etc.

A wire guide (centering plug) is provided with means for advancing this wire through the needle and then into the lumen, said wire bending to the configuration and path of the lumen. The guide wire is carried in a closed and flexible sheath or lay-flat tube that prevents contamination of the wire and the pathway into the vessel. This flexible sheath is secured to the centering plug which is secured to the needle hub. The guide wire may be color-coded to show placement advance of the guide wire to the end of the needle.

After penetration of the vessel by the needle end and a flashback is perceived, the guide wire is first advanced to the end of the needle and then by careful manipulation is further advanced into the vessel. After the desired advancement into the vessel, the guide wire is used to allow the catheter to be slid along the guide wire generally before the needle is withdrawn from the body opening. The hub of the catheter is separated from the hub of the needle and then said needle, with guide wire, centering plug and bag, is discarded, leaving the catheter in place in the artery or vein.

In the embodiments to be shown and more fully described hereinafter, it is to be noted that the guide wire has its rear end secured to the terminal or distant end of the bag so that with grasping and manipulating of the guide wire by a thumb and finger of the user, an advancing of the guide wire results in an accordion-like condition of the bag. This bag is made of a lay-flat plastic tubing generally about one- to two-thousandths of an inch in thickness and having no rigidity. This bag is of transparent plastic much like that used for a wrap of sandwiches, etc. The guide wire used in this device is sufficiently flexible to easily follow a vein or artery and therefore in the smaller catheter sizes generally cannot be advanced by grasping the distal end, but must be advanced near the centering plug by the practitioner. This bag, while protecting the guide wire and other elements and maintaining sterility, allows the practitioner to manipulate the guide wire and establish a feel of the advancing guide wire substantially as if the bag was absent. This procedure or practice has not been available in the known prior art devices.

The lay-flat tubing enclosure may restrain the guide wire without a securing of the distal end of guide wire. The distal end of the tubing is sealed and the guide wire enclosed within this tubing which is usually of such a small diameter extent that positioning of the guide wire within may be adequate with a sealing of this distal end. If in shipping or otherwise the guide wire is accidentally advanced into the needle, this circumstance can be rectified by the user who, just prior to use, moves the mispositioned guide wire into the centering plug, thus opening the flashback indicator. Where the guide wire is not secured, accordionizing usually does not occur. Accordionizing is present in FIGS. 7, 8 and 9 when the distal end of the guide wire is secured to the distal end of the tubing.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen embodiments of closed catheter systems with a catheter and a guide wire for placement in a lumen as adopted for use in penetration of a lumen and showing a preferred means for bending and advancing a catheter by use of a guide wire. These specific embodiments have been chosen for the purpose of illustration and description as shown in the accompanying drawings wherein:

BRIEF DESCRIPTION OF THE DRAWINGS

FIG. 1 represents an exploded isometric view of the components as used for the catheter with guide wire of this invention;

FIG. 2A represents a sectional side view, partly diagrammatic, of the device of FIG. 1 as assembled and ready for use in a patient;

FIG. 2B represents the sectional side view of the device of FIG. 2A, but with the guide wire advanced to substantially its extended limit;

FIG. 2C represents the sectional side view of FIG. 2B, but with the catheter and hub separated from the needle, centering plug, attached envelope and guide wire;

FIG. 2D represents a sectional view taken on the line 2D—2D of FIG. 2A and looking in the direction of the arrows;

FIG. 3A represents a partly diagrammatic sectional view in an enlarged scale and depicting one configuration of a centering plug;

FIG. 3B represents a partly diagrammatic sectional side view of yet another centering plug having modifications which include providing vent means therein;

FIG. 3C represents a partly diagrammatic side sectional view similar to that of FIG. 3B, but with the molding of porous plastic;

FIG. 3D represents a partly diagrammatic sectional side view of a centering plug adapted to receive and retain a tubular sleeve extending from the needle to the centering plug, with the sleeve having a blood discharge aperture;

FIG. 4A represents a fragmentary plan view, partly diagrammatic, and showing a method of sealing a distal end of the bag and retaining the end of the guide wire therewith;

FIG. 4B represents a plan view showing an end seal of the bag and guide wire end, this view also showing the assembled device with alternate constructions of components;

FIG. 4C represents a fragmentary plan view, partly diagrammatic, and showing the sealing of the bag end and guide wire with a V-shaped seal and with the end of the guide wire having an applied member portion;

FIG. 5A represents a plan view of an assembled device and showing the end of the guide wire bent into a hook and with a double heat-seal of the bag;

FIG. 5B represents a side view, partly in section and diagrammatic, and showing the tubular connecting member as secured by crimping to the needle and providing a heat-shrunk band that maintains the end of the bag to both the centering plug and the skirt portion of the needle hub;

Figure 6:
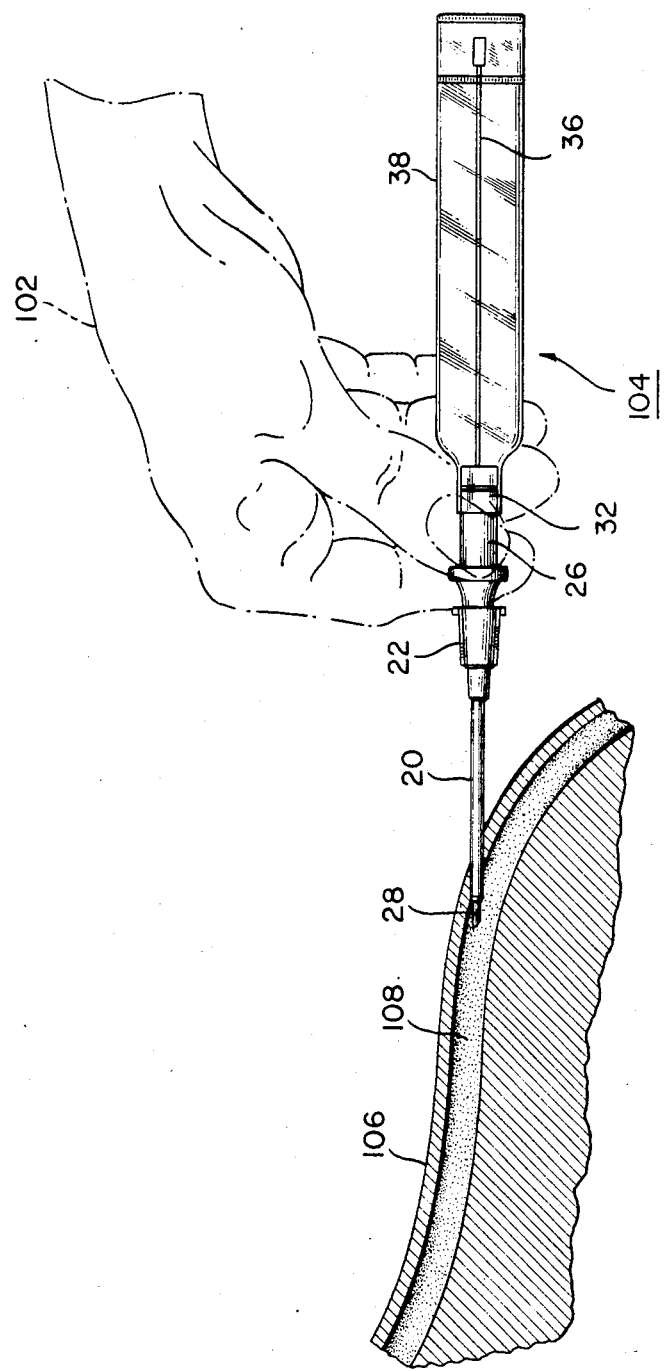
FIG. 6 represents a diagrammatic showing of the device as manipulated for penetration of the skin of a patient by the needle of the device.

In the following description and in the claims, various details are identified by specific names for convenience. These names are intended to be generic in their application. Corresponding reference characters refer to like members throughout the several figures of the drawings. Structural details may be modified without departure from the concept and principles of the invention and the invention may be incorporated in other structural forms than shown.

EMBODIMENT OF FIG. 1

In FIG. 1 there is depicted the catheter with guide wire of this invention in an exploded view to illustrate the relationship of components. As shown in this FIG., there is provided a conventional protector 10 which is usually of an extruded plastic. A flexible catheter with a hub is generally identified as 12 and this essential component is also quite conventional. A needle and hub, generally identified as 14, has the hub with at least the rearwardly projecting skirt portion of a clear or translucent material to provide blood flow indication. A guide wire bag and centering plug is generally identified as 16. The projecting of the needle into the rear of the hub in the arrangement of 14 is shown later in two arrangements. The guide wire and centering plug is shown in four arrangements although variations thereof may be devised. The lay-flat bag enclosure of 16 is shown in three means of securing, but retention of the guide wire at the end of this supple bag may be provided in several ways.

EMBODIMENT OF FIG. 2A

In FIG. 2A is shown a sectional view of the assembled components of FIG. 1 with the protector 10 removed. This sectional view shows the device ready for use with a patient. A flexible catheter 20 is conventional and is attached to a holded hub 22 with a tapered cavity 23 formed therein. Grasping ear or a flange portion 24 is provided on this hub to provide a luer lock connector. Immediately to the right is a needle hub, generally identified as 26. This needle hub is molded of substantially translucent or clear plastic. A needle 28 of metal (usually stainless steel) is of hollow tubing and is sharpened at the entering end. This needle is secured in the molded hub and extends into the cavity 30 formed in said hub. This cavity 30 is tapered to provide a seating and securing of a centering member or plug 32 formed with a tapered central passageway 34. The front end portion of this plug 32 is formed with an enlarged circular cavity into which the rear end of the needle 28 extends so as to be immediately proximate to the tapered passageway 34.

Still referring to FIG. 2A, it is to be noted that a guide wire 36 is carried within a very supple bag or envelope 38 which is attached to the rear of the centering plug 32 as by heat-sealing or a shrink-wrap band. The rear end of this bag 38 is closed by a heat-seal 40 or the like which may also be used to retain the distal end of the guide wire 36. As seen in FIG. 2A, the left end of the guide wire is just ready to enter the end of the needle 28.

EMBODIMENT OF FIG. 2B

In FIG. 2B the device is shown with the guide wire 36 extending beyond the needle 28 and catheter 20. It is to be noted that movement of the guide wire is achieved only by grasping the guide wire through the bag 38 near the centering plug 32. This wire is grasped by the practitioner's thumb and finger and usually advanced in small increments or steps. The bag 38 during this forward advancement of the guide wire in the needle 28 is in an accordion-like condition. The length of the guide wire and advanced length are a matter of selection. The advancement of the guide wire within the needle effectively halts the flow of blood through the needle. The entering end of the guide wire is formed so as to not effect a puncture of the lumen of the patient's vein or artery.

EMBODIMENT OF FIG. 2C

In FIG. 2C the device of FIG. 2A is shown with the catheter 20 and hub 22 in substantially the separated condition. It is assumed that the guide wire has been advanced to its desired limit, after which the flexible catheter has been advanced along the guide wire into the lumen in the patient. The advancement of the catheter requires disassembly of the catheter and hub from the needle and guide wire and associated components. The withdrawal from the catheter 20 and subsequent discarding of the needle 28, attached hub 26, centering plug 32, bag 38 and guide wire 36 allows blood flow through the catheter 20, hub 22 and tapered socket 23. Connection to another device or accessory is achieved rapidly.

EMBODIMENT OF FIG. 2D

In FIG. 2D a sectional view of the bag 38 and the guide wire 36 is shown. This view is taken on the line 2D—2D of FIG. 2A and illustrates that the lay-flat bag 38 is close to the guide wire. The bag is made of thin and very flexible plastic so that "feel" of the guide wire through the sides of the bag does not appreciably change the feel of the guide wire in the artery of a patient.

EMBODIMEMT OF FIG. 3A

In FIG. 3A there is shown a centering plug which depicts an arrangement for fitting into the tapered recess 30 in the needle hub, generally identified as 26. In this showing, the centering plug is generally identified as 46 and is characterized as having a tapered end portion 48 with a small forward end portion 50 in which there is molded or formed a circular recess 52. This recess is larger than the needle 28 as carried in the molding 26. A small diameter passageway 54 for guide wire 36 extends from recess 52 to a tapered guideway 56 extending to the rear end of centering plug 46. The skirt portion 58 is shown with an overhanging shroud 60 that provides a receiving groove 61 for the front end of bag or envelope 38 of FIG. 2A. This showing is in enlarged scale to more clearly show the interrelated components of the device.

EMBODIMENT OF FIG. 3B

In FIG. 3B the centering plug is shown with slight modifications, but the general purpose is the same. This plug is generally identified as 62 and, as in FIG. 3A, has a tapered end portion 48. This end portion has a reduced forward portion 63, much like 50 above, and in this forward portion is a circular recess 52. Rather than a complete enclosure, there is provided a radial slot or groove 64 providing a fluid flow path or means from the end of the needle 28 to the outer portion of the centering plug. A tapered recess 66 is formed in this plug, but it is noted that this tapered recess is with a smaller included angle and terminates at the rear end of recess 52 and that there is no passageway 54 (FIG. 3A) in this embodiment. A vent conduit 68 is provided in this molding and a slot 70 provides a further communication of the chamber of the bag 38 with the needle hub cavity. A flange 72 provides a stop for positioning the bag on a skirt portion 74.

EMBODIMENT OF FIG. 3C

In FIG. 3C the centering plug of FIG. 3B is depicted but, rather than a vent, the plug (generally identified as 78) is molded of a porous plastic through which air may flow under a small differential in pressure. This plug 78, except for the being molded of porous plastic, is substantially like the plug of FIG. 3B in that the tapered portion 48 and the small forward portion 50 are like those noted above. The circular recess 52 is proximate the rear end of the needle 28, but does not obstruct a small flow of blood from a penetrated artery or vein.

Flange 72 on skirt portion 74 provides a stop for the positioning of a bag 38 on plug 78. The tapered recess 66 for the guidance of the guide wire 36 is like in FIG. 3B, but a configuration such as in FIG. 3A may be used and is contemplated.

EMBODIMENT OF FIG. 3D

In FIG. 3D a centering plug, generally identified as 80, is much like the plug of FIG. 3A but, rather than the exit end of the needle 28 residing in recess 52, the needle is made so as to extend only a short distance into the cavity 30 formed in the needle hub 26 as seen in FIG. 2A. Rather than a recess 52 as in FIG. 3C, this plug 80 is made with a passageway 82 that is sized to tightly retain tubular member 84. This tubular member is formed with an aperture 86 providing a discharge path for blood which indicates the penetration of the lumen of a patient's artery or vein. Conventionally, this length of tubing 84 is of metal or rigid plastic, and by a crimp means or adhesive is retained on this needle for initial assembly. Assembly, using retention of the tubing 84 in the centering plug 80, is also contemplated as it is only required that the tubing 84 be retained in position during assembly and particularly to preclude accidental closing of the aperture 86.

RETENTION OF GUIDE WIRE AS IN FIGS. 4A, 4B AND 4C

In FIGS. 4A, B and C there is depicted means for securing the distal or left end of the guide wire 36 to the end of the bag 38. It is desired that a closing of the rear of this bag be achieved and at the same time the guide wire end be secured. Many methods may be provided and among these are illustrated three methods of securing.

EMBODIMENT OF FIG. 4A

In the fragmentary view of FIG. 4A it is contemplated that the guide wire 36 is formed into a curl 90 which is secured by a heat-seal 44 of the bag. This securing insures that when the guide wire 36 is advanced, the bag 38 is in an accordion-like condition as in FIG. 2B.

EMBODIMENT OF FIG. 4B

In the fragmentary view of FIG. 4B is shown the guide wire 36 retained in the heat-sealed end closing 40 as shown in FIG. 2A. An internal sleeve 42 is retained by another seal 44.

EMBODIMENT OF FIG. 4C

In the fragmentary view of FIG. 4C is shown the guide wire 36 having an end plug or similar device 94. A seal 96 is shown which may be in a V-shape or similar. It is only necessary that the end portion of the guide wire 36 be secured in this sealed bag 38.

EMBODIMENTS OF FIGS. 5A AND 5B

In FIG. 5A the flexible bag 38 is shown with the guide wire 36 having a hook 90 as in FIG. 4A. The retention of this hook end is by a V-type seal 96 as in FIG. 4C, but, as seen in this view, the V-seal is shown in an opposite attitude. The terminal end 97 of the bag is also indicated as sealed. It is to be noted that a heat-sealed or shrink-wrap band 98 is provided and extends sufficiently to retain the bag to the centering plug and also to retain the bag to the needle hub.

In FIG. 5B there is shown, partly in section and partly diagrammatic, a view using the showing of FIG. 3D. The needle 28 has a short portion that extends rearwardly into the cavity 56. The tubular member 84 is slid onto this needle end and secured by cement, etc. The guideway 82 receives this tubular member and an entering end of the guide wire is fed into this tubular member 84. The entering end of the guide wire provides a fluid stop to the flow of blood when penetration of the lumen has been made.

EMBODIMENT OF FIG. 6

As seen in FIG. 6, a hand 102 is shown grasping the device, generally identified as 104, and with the usual manipulation the sharpened end of needle 28 is advanced through the skin 106 and into the lumen 108 of the patient. The catheter 20 is also advanced as the needle is advanced. Bag 38 with the guide wire 36 therein is also depicted. Penetration of the lumen 108 by the needle 28 is determined by blood flow through the hollow needle into the needle hub 26. No matter the centering plug arrangement as in FIGS. 3A, 3B, 3C or 3D, discussed and described above, the proximate end of the guide wire 36 in the centering plug retards the flow of blood into the bag 38. As the guide wire 36 is advanced into the needle, the flow of blood is stopped.

EMBODIMENT OF FIG. 7

Figure 7:
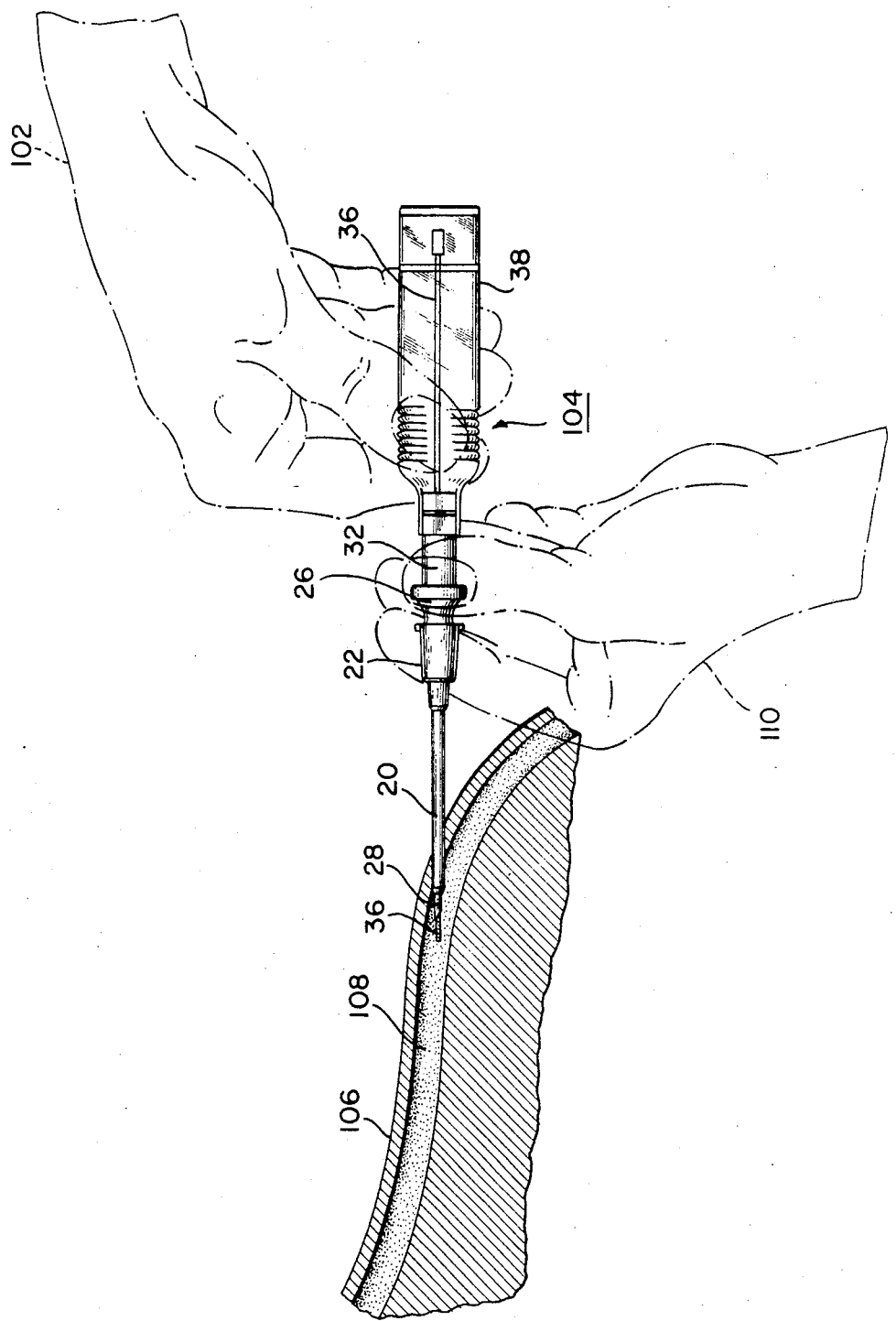
FIG. 7 represents the diagrammatic view of FIG. 6, but with an additional hand used for advancing the guide wire by "feeling" the wire through the thin walls of the bag, the guide wire as shown just beginning to be advanced into a lumen.

In FIG. 7 the device of FIG. 6 is shown, with the needle hub 24 and the centering plug 26 substantially in the position of FIG. 6. The catheter hub 22 and centering plug 26 are grasped by the other hand, generally identified as 110, which retains the catheter and centering plug. The guide wire 36 is seen as just emerging from the end of the needle 28. The advancement of the guide wire in the hollow needle has halted the flow of blood. The guide wire is advanced by "feel" by the practitioner. As indicated, the guide wire 36 is grasped between the thumb and fingers through the sides of the bag 38 and advanced very carefully into the lumen 108. In FIG. 2D the relationship of the bag side walls 38 to the guide wire 36 is depicted.

EMBODIMENT OF FIG. 8

Figure 8:
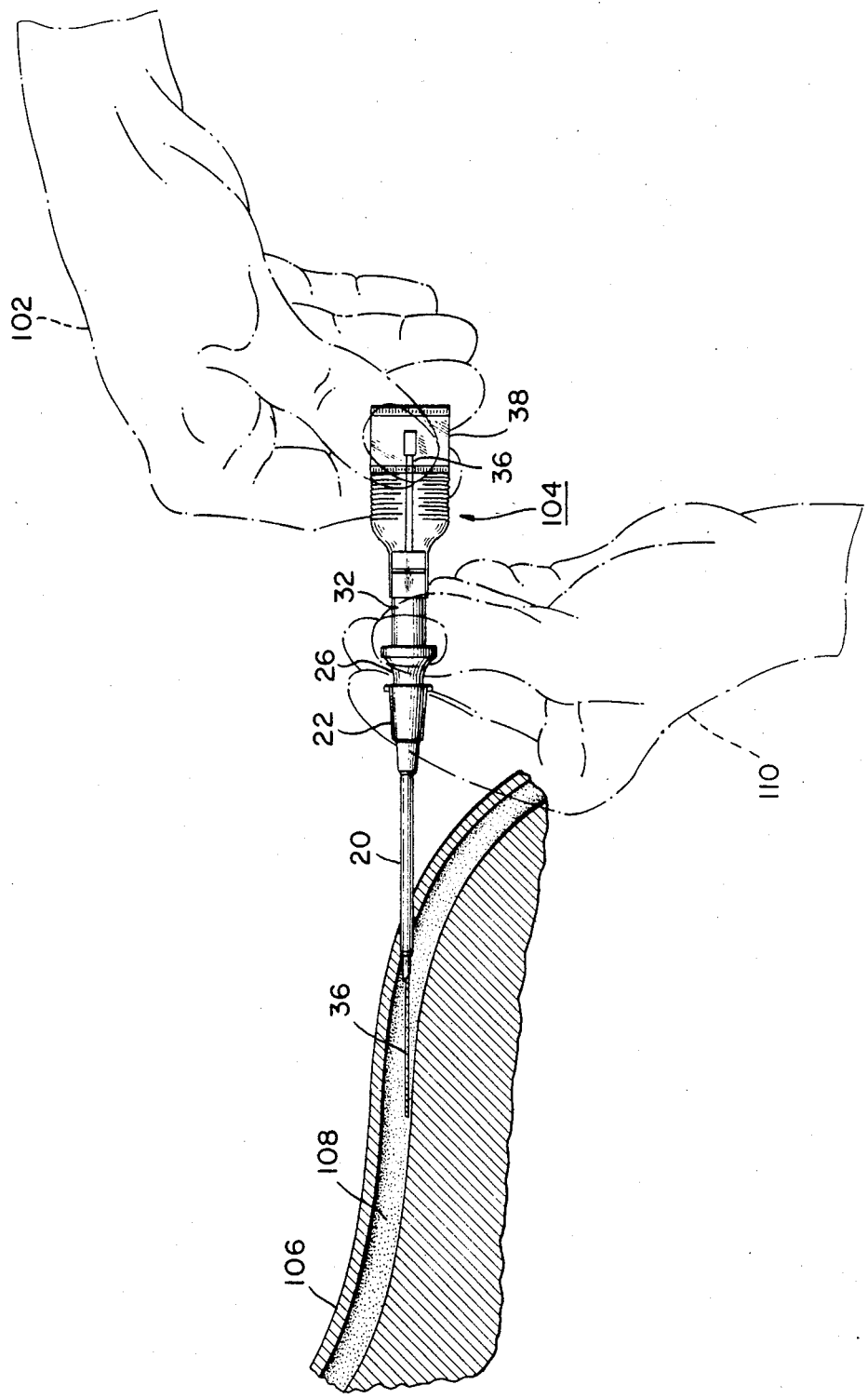
FIG. 8 represents the diagrammatic view of FIG. 7, but with the guide wire advanced to substantially its maximum extent into a lumen of the patient.

Referring next to the diagrammatic showing of FIG. 8, the device is essentially as in FIG. 7, but the guide wire 36 has now been advanced into the lumen 108 about the desired extent. The guide wire may bend to follow the lumen and the advancement of the guide wire causes the bag 38 become accordion-like ahead of the fingers and thumb of hand 102. The bag 38 and guide wire 36, as seen in this FIG. 8, are merely a matter of illustration as configuration are a resulting use of the device and every use usually results in a different configuration. The shape of the bag 38 is not a matter of patentable distinction. This arrangement is similar to that seen in FIG. 2B.

EMBODIMENT OF FIG. 9

Figure 9:
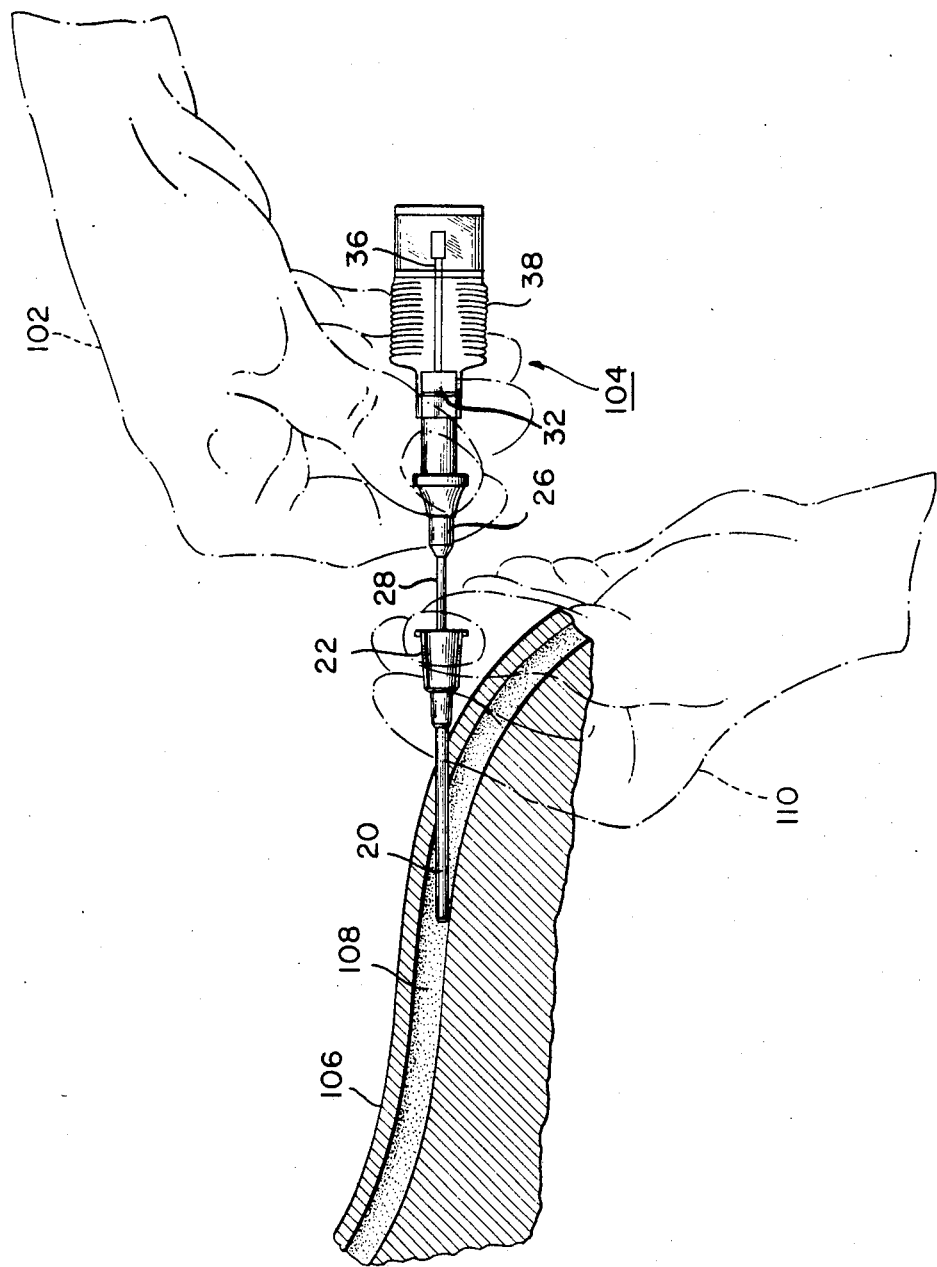
FIG. 9 represents the diagrammatic view of FIG. 8, but with the catheter and hub now in position with the needle, guide wire, centering plug and bag now ready for removal and discarding.

Referring next, and finally, to FIG. 9, the catheter 20 has been slid off the needle and, using the guide wire for placement, has been advanced into the lumen 108 until the catheter hub 22 is against or near the skin 106 of the patient. The needle hub 26 and centering plug 32 are grasped by the hand 102 and separation is made. The needle 28, needle hub 26, centering plug 32, guide wire 36 and bag 38 are now discarded as a unit since they have served their purpose and are now contaminated.

The catheter hub 22 is now connected to associated components, not shown. Such components may be an IV delivery system and the like. This separation is similar to that depicted in FIG. 2C.

USE AND OPERATION

The catheter with guide wire of this invention anticipates the use of a guide wire to advance and position a flexible catheter in the lumen of the patient. As the catheter is of very flexible material, advancement (pushing) into a lumen is often difficult so that a guide wire is used as a guide. After placing the catheter, the rest of the device is surplus so discarding is contemplated. Reuse of the rest is not practical as contamination has occurred with the flow of blood from the patient.

The catheter and hub are very conventional. The protector cap 10 is made to suit the device which may have needles from sixteen to twenty-two gauge, with the needle length and size a matter of selection. The construction of the centering plug 32 establishes the projection of the needle 28 into the cavity 30 of the needle hub 26. Manufacturing design and preference establishes the centering plug construction. Where the needle is not connected by a tubular portion 84 to the centering plug, the needle is made to just enter recess 52 formed in the centering plug. This recess is greater than the needle diameter so that blood from the penetration of the lumen flows through the needle into this recess and then into the cavity 30. The rearwardly-extending skirt portion of the needle hub 26 is sufficiently translucent or substantially transparent to show to the practitioner by the presence of blood that the lumen has been penetrated. The guide wire 36 in the centering plug acts as a stop to flow of blood into the bag 38. If any blood does pass by the guide wire, it is quite minimal but may be used as an indicator.

The centering plug may or may not have a vent for allowing any air in the bag 38 during manipulation to be discharged into the cavity 30. In like manner, this vent allows the inflow of blood into cavity 30 to not be blocked by trapped air in this cavity. The advance of the guide wire into the needle substantially blocks blood flow. After penetration of the lumen 108 as in FIG. 6, the guide wire 36 is advanced by the practitioner as in FIG. 7. Bag 38 is made from a thin, supple plastic so that gripping the guide wire through the side walls of the plastic bag does not appreciably change the "feel" of the guide wire as it is moved into the lumen. This "feel" control is very important as this permits the practitioner to advance the guide wire and, with controlled movements, avoid puncturing the wall of the lumen. The bag 38 is conventionally made from extruded "lay-flat" tubing having a wall thickness of one- to three-thousandths of an inch. This tubing is sized to be a slide fit on the outer diameter of the centering plug. The tapered guideway is configured so that the guide wire is easily placed in the centering plug and is brought proximate the end of the needle 28 so that passage into and through the needle is achieved easily.

The closing of the distal end of the bag or envelope 38 is usually made by heat-sealing, but adhesive is also contemplated. This closing of the end achieves two purposes. A first purpose is to maintain sterility after closing. Sterilizing is by known and approved means. The other purpose is to retain the end of the guide wire so that this wire is positioned, more or less, at the axis of the bag. The retaining of this guide wire end prevents unwanted movement of the guide wire and possible puncturing of the bag by the wire end. Several means of retaining this guide wire are shown, but other means may be employed and the configuration of the end closing and wire retention are merely a matter of design.

The above depicted and described apparatus suggests a method of making, assembling and using the catheter with guide wire. This method includes the step of:

(a) supplying a hollow needle of a determined length and having a sharpened entering and an exit end;

(b) securing axially a needle hub to said needle and positioning said hub at a selected distance from the sharpened end, and forming said hub with a forward contoured end and having a skirt portion providing an interior cavity which is open to the rear thereof;

(c) providing a flashback indicating means at or near the exit end of the needle and in flow communication with said needle so as to indicate an initial penetration of a wall of said blood vessel;

(d) forming a flexible catheter with a through bore and slideable on and along the outer diameter of the needle, said catheter having an entering end sized to be easily inserted with the sharpened end of the needle into the lumen of the vessel, and fixedly securing the other end of the flexible catheter in a hub member which is formed so as to be mounted on the contoured forward end of the needle hub;

(e) providing, forming and positioning a centering plug so that its forward end is retained within the skirt portion of the needle hub and forming in said centering plug a through guideway and positioning and terminating said guideway so that said guideway is substantially in alignment with the bore of the needle and proximate to the exit end of said needle;

(f) providing a guide wire of a selected length and having a blunted entering end sized to be a slide fit in the bore of the needle and advancing this wire by manipulation to and through the bore of the needle, and as this wire is advanced it exits the sharpened end of the needle and, with further advancement, the practitioner causes the advancing wire to follow the lumen path of the blood vessel, and (g) providing and securing to the open rear end of the needle hub a flexible enclosure from lay-flat tubing, this tubing of a determined length and at least partially encapsulating the guide wire and retaining the distal end of said guide wire at or near the unsecured end of the tubing and sealing this unsecured end of the tubing.

In the depicted apparatus, the front or entering end of the catheter 20 is shown with an angled contour. This is usually produced by a heated die to insure a tight fit of the catheter on the shank of the needle 28. The securing of the fore end of the bag or envelope 38 to the needle hub 26 is by known means including heat-sealing, cement or by an added shrink-band. The fore end of the envelope is secured in such a manner that the interior of the bag or envelope 38 is sealed and can and is sterilized before shipping and use in a patient. The sealing of the rear end of the envelope 38 also secures the distal end od the wire 36 and many methods of securing may be provided. As depicted, the double heat-seal 40 and 42 not only insures the sealing of the envelope but, with an added sleeve portion 44 is secured to the distal end of the wire 36, the inner heat seal, as seen in FIGS. 3 and 4, provides for the retention of the wire during manipulation and separation.

To the extent applicable, the disclosure in U.S. Pat. No. 4,525,157, as issued June 25, 1985, is incorporated by reference into the above application.

Terms such as "left," "right," "up," "down," "top," "front," "back," "in," "out" and the like are applicable to the two embodiments shown and described in conjunction with the drawings. These terms are merely for the purposes of description and do not necessarily apply to the position in which the catheter with guide wire may be constructed or used.

While particular embodiments of the apparatus and method of constructing and using have been shown and described, it is to be understood that the invention is not limited thereto and protection is sought to the broadest extent the prior art allows.

What is claimed is:

1. A closed catheter system for the introduction and placement of a flexible catheter in the lumen of a blood vessel and using the advancement of a wire into said lumen to guide the flexible catheter as said catheter is advanced and positioned in said lumen, said closed catheter system including:
    (a) hollow needle of a determined length and having a sharpened entering end and an exit end;
    (b) a hub axially secured and mounted to said needle and positioned at a selected distance from the sharpened end of said needle, this hub having a skirt portion providing an interior cavity which is open to the rear thereof, this hub having a contoured forward end;
    (c) a flexible catheter formed with a through bore and slideable on and along the outer diameter of the needle, said catheter having an entering end sized to be easily inserted with the needle into the lumen of the vessel and with the other end of said flexible catheter attached to a hub adapted to be removably mounted on the contoured forward end of the needle hub;
    (d) a centering plug within the needle hub with means for retaining said centering plug within the interior cavity of the needle hub, this centering plug having a through guideway positioned and terminating so the exit end of said guideway is substantially in alignment with the bore of the needle;
    (e) a wire positioned and sized so as to be slide fit in the bore of the needle, said wire disposed to be advanced by manipulation to and through said guideway and bore of the needle, and as the wire is advanced and exits the sharpened entering end of the needle, this wire is caused to follow the lumen path of the blood vessel, and
    (f) a lay-flat tube enclosure providing an envelope having a distal end sealed to at least partially encapsulate and restrain this distal end of the wire, this enclosure attached at its other end to the guide assembly and providing therewith a sealed enclosure of the wire.

2. A closed catheter system as in claim 1 in which there is provided a flashback indicating means disposed at or near the exit end of the needle and in flow communication with said needle so as to indicate an initial penetration of a wall of said blood vessel.

3. A closed catheter system as in claim 2 in which the needle extends into the interior cavity of the needle hub and the forward end of the centering plug is formed with a recess which is larger than the needle diameter and provides a flow path from the exit end of the needle and into the skirt portion of the needle hub.

4. A closed catheter system as in claim 3 in which the centering plug is also formed with a tapered recess whose small portion terminates at a guideway sized to slideably guide the wire and with this guideway terminating at the recess in the forward end of said centering plug.

5. A closed catheter system as in claim 4 in which the centering plug is formed with a shroud, with a receiving tubular groove into which the forward end of the envelope may be and is secured.

6. A closed catheter system as in claim 4 in which the centering plug is formed with a vent from the enclosure envelope to the interior cavity formed in the needle hub.

7. A closed catheter system as in claim 6 in which the centering plug is also formed with an outwardly-extending flange portion providing a shoulder stop for the front end of the envelope.

8. A closed catheter system as in claim 3 in which the recess in the forward end of the centering plug is provided with a transverse groove providing a fluid flow path from the recess to the outer surface of the centering plug.

9. A closed catheter system as in claim 8 in which said recess is substantially cylindrical.

10. A closed catheter system as in claim 3 in which the centering plug is molded of porous plastic that is hydrophilic to exclude the passage of blood produced as a result of the puncturing of the vessel.

11. A closed catheter system as in claim 10 in which the recess in the forward end of the centering plug is provided with a transverse groove providing a fluid flow path from the recess to the outer surface of the centering plug.

12. A closed catheter system as in claim 2 in which the needle extends into the interior cavity and there is provided a tubular member or sleeve slideably retained on this extending needle portion, with this sleeve having its exit end portion secured in a passageway formed in the centering plug, and in this sleeve is provided an aperture formed in the side wall of the sleeve and providing therewith a fluid pathway from the needle into said interior cavity of the needle hub.

13. A closed catheter system as in claim 12 in which the sleeve is of right material, with this sleeve secured to the needle as by cement, and the centering plug is formed with a tapered guideway extending from the rear end of the centering plug so as to terminate said adjacent sleeve.

14. A closed catheter system as in claim 12 in which the sleeve is of rigid material and with this sleeve secured to the exit end of the needle by at least one crimp.

15. A closed catheter system as in claim 2 in which the wire is secured to the distal end of the tube enclosure as by forming the distal end of the wire into a curl and securing this curled end with a sealing of this distal end of the enclosure.

16. A closed catheter system as in claim 2 in which the wire is secured to the distal end of the tube enclosure by securing an end sleeve to the wire end and securing this end sleeve and wire by an interior seal proximate to said end sleeve and interior thereof and sealing the distal end of the tube enclosure to maintain the exclusion property of the interior of the enclosure.

17. A closed catheter system as in claim 15 in which the interior seal of the tube enclosure is V-shaped, with the apex of the "V" substantially at the retaining location of the wire.

18. A closed catheter system as in claim 16 in which the sealing of the distal end of the enclosure is by a heat seal of the lay-flat tube enclosure.

19. A closed catheter system as in claim 2 in which at least the skirt portion of the needle hub is of molded plastic and is at least translucent.

20. A method for constructing a closed catheter system adapted for placing a flexible catheter into the lumen of vessel and using the advancement of a guide wire into said lumen to guide the flexible catheter as it is advanced and positioned in said lumen, said construction method including the steps of:
   (a) supplying a hollow needle of a determined length and having a sharpened entering and an exit end;
   (b) securing axially a needle hub to said needle and positioning said hub at a selected distance from the sharpened end, and forming said hub with a forward contoured end and having a skirt portion providing an interior cavity which is open to the rear thereof;
   (c) providing a flashback indicating means at or near the exit end of the needle and in flow communication with said needle so as to indicate an initial penetration of a wall of said blood vessel;
   (d) forming a flexible catheter with a through bore and slideable on and along the outer diameter of the needle, said catheter having an entering end sized to be easily inserted with the sharpened end of the needle into the lumen of the vessel, and fixedly securing the other end of the flexible catheter in a hub member which is formed so as to be mounted on the contoured forward end of the needle hub;
   (e) providing, forming and positioning a centering plug so that its forward end is retained within the skirt portion of the needle hub and forming in said centering plug a through guideway and positioning and terminating said guideway so that said guideway is substantially in alignment with the bore of the needle and proximate to the exit end of said needle;
   (f) providing a guide wire of a selected length and having a blunted entering end sized to be a slide fit in the bore of the needle and advancing this wire by manipulation to and through the bore of the needle, and as this wire is advanced it exits the sharpened end of the needle and, with further advancement, the practitioner causes the advancing wire to follow the lumen path of the blood vessel, and
   (g) providing and securing to the open rear end of the needle hub a flexible enclosure from lay-flat tubing, this tubing of a determined length and at least partially encapsulating the guide wire and restraining the distal end of said guide wire at or near the unsecured end of the tubing and sealing this unsecured end of the tubing.

21. A method for constructing a closed catheter system adapted for placing a flexible catheter as in claim 20 which further includes extending the needle into the interior cavity of the needle hub and forming in the forward end of the centering plug a forced recess which with the centering plug in mounted condition is slightly distant from the exit end of the needle and with this formed recess larger than the needle diameter, therewith providing a flow path from the exit end of the needle and into the skirt portion of the needle hub.

22. A method for constructing a closed catheter system adapted for placing a flexible catheter as in claim 21 which further includes forming the centering plug with a tapered recess and configuring said recess so that the small portion terminates at a guideway sized to slideably guide the wire and with this guideway terminating at the recess in the forward end of said centering plug.

23. A method for constructing a closed catheter system adapted for placing a flexible catheter as in claim 20 which further includes forming the centering plug with a vent from the lay-flat enclosure envelope to the interior cavity formed in the needle hub.

24. A method for constructing a closed catheter system adapted for placing a flexible catheter as in claim 23 which further includes forming the centering plug with an outwardly-extending flange portion providing a shoulder stop for the front end of the envelope.

25. A method for constructing a closed catheter system adapted for placing a flexible catheter as in claim 21 which further includes forming in the recess in the forward end of the centering plug a transverse groove providing a fluid flow path from the recess to the outer surface of the centering plug.

26. A method for constructing a closed catheter system adapted for placing a flexible catheter as in claim 21 which further includes molding the centering plug of porous plastic that is hydrophilic to exclude the passage of blood produced as a result of the puncturing of the vessel.

27. A closed catheter system and device for the introduction and placement of a flexible catheter in the lumen of a blood vessel and using the advancement of an enclosed wire into said lumen to guide the flexible catheter as said catheter is advanced and positioned in said lumen, this device retaining the "feel" properties of an Intravenous Catheter without attached guide wire during initial penetration, said closed catheter system including
   (a) a conventional Intravenous Catheter (I.V.) characterized as having:
      (a-1) a hollow needle of a determined length and having a sharpened entering end and an exit end;
      (a-2) a hub axially secured and mounted to said needle and positioned at a selected distance from the sharpened end of said needle, this hub having a skirt portion providing an interior cavity which is open to the rear thereof, this hub having a contoured forward end;
      (a-3) a flexible catheter formed with a through bore and slideable on and along the outer diameter of the needle, said catheter having an entering end sized to be easily inserted with the needle into the lumen of the vessel and with the other end of said flexible catheter attached to a hub adapted to be removably mounted on the contoured forward end of the needle hub;
   (b) a centering plug contiguous to the needle hub with means for retaining said centering plug within the interior cavity of the needle hub, this centering plug having a through guideway positioned and terminating so the exit end of said guideway is substantially in alignment with the bore of the needle;
   (c) a flexible wire positioned and sized so as to be a slide fit in the guideway of the centering plug and bore of the needle of the conventional Intravenous Catheter, said wire disposed to be advanced by manipulation to and through said guideway in the centering plug and the bore of the needle and, as the wire is advanced, a blunt (non-sharp) entering end exits the sharpened end of the needle, this advancing wire caused to follow the path of the lumen of the blood vessel, and (d) a flexible enclosure from lay-flat tubing and having one end attached to the open rear end of the needle hub, this tubing at least partially encapsulating the guide wire, to achieve a closed system, said flexible enclosure and enclosed wire maintaining a balanced catheter when center of gravity is within the confines of the conventional Intravenous Catheter to be able to "feel" the wire as it is advanced.

* * * * *